United States Patent [19]

Bamberg et al.

[11] Patent Number: 4,898,731
[45] Date of Patent: Feb. 6, 1990

[54] ANTIBIOTIC COMBINATIONS OF PENICILLINS

[75] Inventors: Peter Bamberg, Zurich, Switzerland; Bertil A. Ekström, Södertälje, Sweden; Ulf E. Forsgren, Södertälje, Sweden; Berndt O. H. Sjöberg, Södertälje, Sweden

[73] Assignees: Astra Läkemedel Aktiebolag; Astra Pharmaceutical Products, Inc., both of Sweden

[21] Appl. No.: 748,268

[22] Filed: Jun. 24, 1985

Related U.S. Application Data

[60] Division of Ser. No. 464,157, Apr. 25, 1974, abandoned, which is a continuation-in-part of Ser. No. 302,423, Oct. 31, 1972, abandoned.

[30] Foreign Application Priority Data

Nov. 1, 1971 [GB] United Kingdom .............. 50675/71

[51] Int. Cl.$^4$ .............................................. A61K 31/43
[52] U.S. Cl. .................................. 424/114; 514/196; 514/197; 514/198
[58] Field of Search ........................................ 424/114

[56] References Cited

U.S. PATENT DOCUMENTS 3,317,389  5/1967  Granatek et al. ................ 424/114

OTHER PUBLICATIONS

Derwent Farm Doc #34108s, Abstracting WL-70164-35-Q, published 5-13-71.
Chemical Abstract 72:109360e (1970).

*Primary Examiner*—Jerome D. Goldberg
*Attorney, Agent, or Firm*—George M. Gould; Bernard S. Leon

[57] ABSTRACT

An antibacterial synergistic composition consisting essentially of a mixture of a penicillin or cephalosporin derivative of the formula

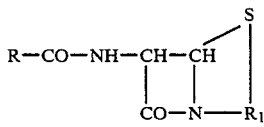

and a penicillin of the formula

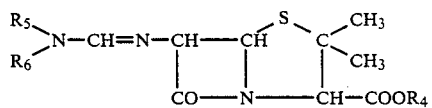

preferably in association with a pharmaceutical carrier.

2 Claims, No Drawings

ANTIBIOTIC COMBINATIONS OF PENICILLINS

This is a division of application Ser. No. 464,157, filed Apr. 25, 1974, abandoned which in turn is a continuation-in-part application of Ser. No. 302,423, filed Oct. 31, 1972, now abandoned.

This invention relates to new antibacterial synergistic compositions containing penicillin derivatives or cephalosporin derivatives, methods for the preparation of such compositions and a method for the treatment of infectious diseases.

In particular, this invention relates to an antibacterial synergistic composition consisting essentially of a mixture of:

(a) a known, clinically useful penicillin or cephalosporin of the formula

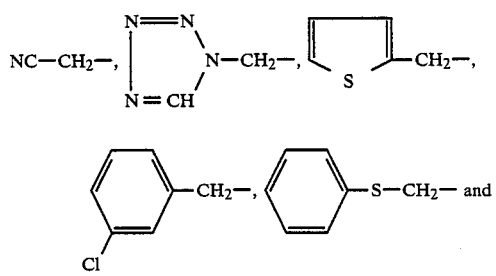

wherein R is a residue of an organic acid, the residue being selected from the group consisting of

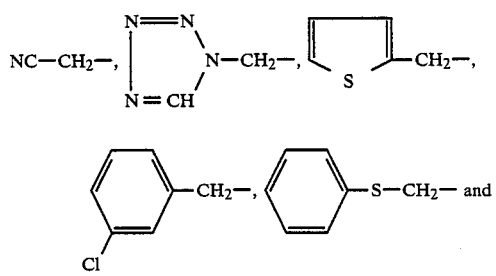

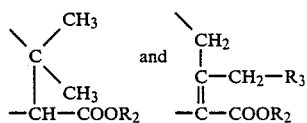

wherein X is selected from the group consisting of —H, —NH$_2$, —N$_3$, —COOH and —SO$_3$H, and wherein R$^1$ is selected from the group consisting of the bivalent radicals

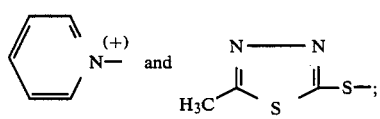

wherein R$_2$ is hydrogen, a pharmaceutically acceptable cation or an in vivo rapidly hydrolyzed pharmaceutically acceptable ester group, and wherein R$_3$ is selected from the group consisting of H—, CH$_3$COO—, N$_3$—,

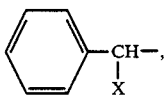

and (b) a known, clinically useful penicillin of the formula

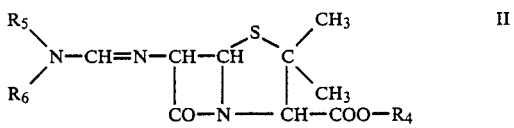

wherein R$_4$ is hydrogen, a pharmaceutically acceptable cation or an in vivo rapidly hydrolyzed pharmaceutically acceptable ester group, and wherein R$_5$ and R$_6$ are lower alkyl groups containing not more than four carbon atoms, or R$_5$ and R$_6$, when taken together with the adjacent nitrogen atom, represent a ring system of the formula

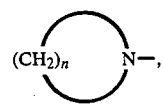

wherein n is 5, 6 or 7.

The above described composition contains the compounds of formula I and II in a weight ratio varying from 10:1 to 1:10, preferably varying from 2:1 to 1:2. Optionally, the composition can be incorporated in a pharmaceutically acceptable carrier.

It has surprisingly been found that by combining a compound with the general formula I with a compound of the general formula II to form the above described composition, the antibacterial activity of both compounds may be greatly enhanced.

A further surprising finding is that bacterial organisms may develop resistance to a combination of compounds of the formula I and II less readily than to either of the compounds alone.

In the formula I above the group R is preferably a group of the formula

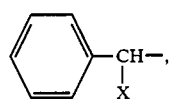

wherein X is —H, —NH$_2$, —N$_3$, —COOH or —SO$_3$H, provided that the compound of the formula I is a penicillin. However, when the compound of the formula I above is a cephalosporin, the group R is preferably a group selected from

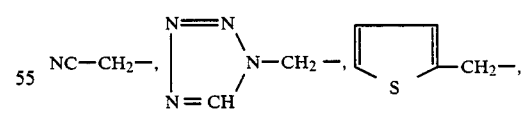

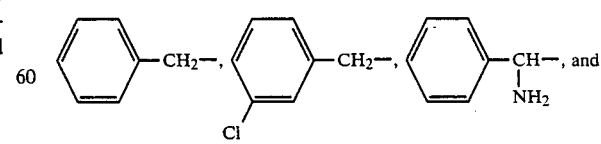

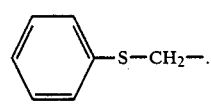

A great number of penicillins and cephalosporins with the general formula I are known to have strong antibacterial activity and such penicillins and cephalosporins have been extensively used for the treatment of infectious diseases caused by Gram-positive and Gram-negative bacteria. In the composition of the invention the preferred compounds of the formula I are the penicillins: benzyl-penicillin, 6-(D-α-aminophenylacetamido)penicillanic acid, 6-(D-α-azidophenylacetamido)penicillanic acid, α-carboxybenzlpenicillin, α-hydroxysulphonyl-benzylpenicillin, and the cephalosporins which are illustrated by the specific combinations of the groups R and $R^3$ in the following table:

| R | $R_3$ | Name |
|---|---|---|
| $NC-CH_2-$ | $CH_3COO-$ | Cephacetrile ($R_2$ = Na) |
| 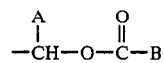 | 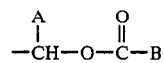 | Cephazoline ($R_2$ = Na) |
| (thienyl)-CH_2- | $CH_3COO-$ | Cephalotine ($R_2$ = Na) |
| (phenyl)-CH(NH_2)- | H— | Cephalexine ($R_2$ = H) |
| (thienyl)-CH_2- | 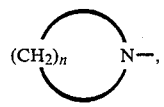 | Cephaloridine ($R_2$ = H) |
| (phenyl)-CH_2- | $CH_3COO-$ | EPC 807/2b ($R_2$ = K) |
| (phenyl)-S-CH_2- | $CH_3COO-$ | EPC 825/1 ($R_2$ = K) |
| (Cl-phenyl)-CH_2- | $CH_3COO-$ | EPC 820/1b ($R_2$ = K) |
| (thienyl)-CH_2- | $N_3-$ | EPC 821/4II ($R_2$ = K) | as well as the corresponding esters and salts of these penicillins and cephalosporins. In the above table, the designations R, $R_2$ and $R_3$ refer to the formula I above.

When the composition of the invention is orally administered, the penicillins or cephalosporins of the formula I may also include such known esters theref which are rapidly hydrolyzed in vivo. Examples of such suitable ester groups i.e. the group $R_2$ in the formula I above, are acyloxy-alkyl groups, e.g. the acetoxymethyl, the pivaloyloxy-methyl or the 1'''-acetoxy-ethyl group; or alkyloxycarbonyloxy-alkyl groups e.g. the ethoxycarbonyloxymethyl or the 1'-ethoxycarbonyloxyethyl group.

The above mentioned suitable ester groups can be described by the formula $$-\underset{A}{\overset{}{C}}H-O-\overset{O}{\overset{\|}{C}}-B$$

wherein A is hydrogen or methyl, and B is alkyl or alkoxy. Preferably the group B should not contain more than four carbon atoms. The preferred meaning of the group A and B is methyl and ethoxy, respectively.

Penicillin and cephalosporin esters of this type are known e.g. from German Patent Applications P 21 44 457.5; P 23 12 041.4; P 23 11 328.2; P 23 12 042.5 and P 23 11 346.4.

Penicillins of the general formula II also exhibit strong antibacterial activity, particularly against Gram-negative organisms. These until recently unknown penicillins have been described in Dutch Patent Application No. 7,016,435 and in British Patent No. 1,293,590.

Examples of compounds of the formula II are 6-[(hexahydro-1H-azepin-1-yl)methyleneamino]-penicillanic acid, 6-[(piperidyl-1)methylenamino]-penicillanic acid, 6-[(hexahydro-1(2H)-azocinnyl)methyleneamino]-penicillanic acid, and 6-[(N-ethyl-N-isopropylamino)-methyleneamino]-penicillanic acid.

In the composition of the invention the preferred penicillins of the formula II are those wherein the groups $R_5$ and $R_6$, when taken together with the adjacent nitrogen atom, represent a ring system of the formula

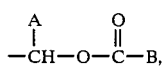

wherein n is 5, 6 or 7. Preferably n is 6.

When the composition of the invention is orally administered also the penicillin of the formula II may be in the form of a known ester thereof, which is rapidly hydrolyzed in vivo. Examples of suitable penicillin esters included in the formula II are those wherein the group $R_4$ is an acyloxy-alkyl group, e.g. the acetoxymethyl, the pivaloyloxy-methyl or the 1'''-acetoxy-ethyl group; or an alkyloxycarbonyloxy-alkyl group e.g. the ethoxycarbonylmethyl or the 1'''-ethoxycarbonyloxyethyl group. Also these ester groups can be described by the formula $$-\underset{A}{\overset{}{C}}H-O-\overset{O}{\overset{\|}{C}}-B,$$

wherein A and B have the meaning given above. Penicillin esters of this type, and included in the formula II, are known e.g. from Dutch Patent Applications No. 7,016,435 and 7,303,434.

Examples of preferred penicillin esters of the formula II are pivaloyloxymethyl 6-[(hexahydro-1H-azepin-1-yl) methyleneamino]penicillanate, acetoxy-methyl 6-[(hexahydro-1H-azepin-1-yl)methyleneamino]penicillanate, pivaloyloxymethyl 6-[(hexahydro1(2H)-azocinnyl)methyleneamino]penicillanate, ethoxycarbonyloxymethyl 6-[(hexahydro-1H-azepin-1-yl)methyleneamino/penicillanate, 1'-ethoxycarbonyloxyethyl 6-[(piperidyl-1)methylene amino]-penicillanate, 1'-acetoxyethyl 6-[(hexahydro-1H-azepin-1-yl)-methyleneamino]penicillanate, 1'-ethoxycarbonyloxyethyl 6-[(hexahydro1(2H)azocinnyl)methyleneamino]-penicillanate, and 1'-ethoxycarbonyloxy-ethyl 6-[(hexahydro-1H-azepin-1-yl)methyleneamino]-penicillanate, and pharmaceutically acceptable salts thereof.

The composition according to the invention can be prepared by various mixing operations well known for the preparation of compositions containing penicillins or cephalosporins. The mixing operations may be accompanied by chemical reactions between the constituents of the new composition. The mixing operations may also be combined with the simultaneous preparation of esters and salts of the penicillins and cephalosporins included in the composition of the invention. It is also to be noted that the new composition according to the invention in some respects can be regarded as one new chemical individual, as the new composition has an antibacterial activity which is unique and widely different from the activity which can be deduced from a calculation based upon the activity of the single constituents.

The composition of the present invention may be administered either orally or by injection. The composition may have optionally incorporated therewith other substances, e.g. pharmaceutically acceptable solid or liquid carriers or diluents and may be in any of the conventional pharmaceutical forms known to the art for pencillin therapy, for example compositions suitable for oral administration, for example tablets, granules, capsules, dispersible powders for the preparation of aqueous dispersions for oral use, solutions, suspensions or emulsions, or compositions suitable for parenteral administration, for example aqueous or nonaqueous solutions or suspensions, or dispersible powders for the preparation of sterile aqueous dispersions, or compositions suitable for topical administration, for example ointments.

The compositions according to the invention shown low toxicity and are well tolerated. In the treatment of bacterial infections in man, the composition of the invention is for example administered in amounts corresponding to 5 to 200 mg/kg/day, of the active ingredients of the composition, preferably in the range of 10 to 100 mg/kg/day in divided dosages, e.g. two, three or four times a day. They are e.g. administered in dosage units containing e.g. 175, 350, 500 and 1000 mg of the active ingredients of the composition.

The following examples illustrate the remarkable antibacterial synergistical effect of the compositions according to the invention.

EXAMPLE 1

In vitro-effect of the combination of 6-(D-α-aminophenylacetamido)penicillanic acid and 6[(hexahydro-1H-azepin-1yl)methylene amino]penicillanic acid The in vitro activity of 6-(D-α-aminophenylacetamido)penicillanic acid (I), 6-[(hexahydro-1H-azepin-1-yl)methyleneamino]penicillanic acid (II) and of a combination (III) of equal parts of the two compounds against clinically isolated enterobacteria was determined in a serial dilution test. Tryptose phosphate broth, containing the appropriate concentrations of the compounds or of the combination of them, was inoculated with $0.5 \times 10^4$–$5 \times 10^4$ organisms of the various microorganisms tested and incubated overnight at 37° C. Minimum inhibitory concentrations (M.I.C.) were taken as the concentrations of the compounds or of the combination at which no visible growth occurred.

| Microorganism | Strain No. | M.I.C. (μg/ml) | | |
|---|---|---|---|---|
| | | I | II | III |
| Coliform | 3/70 | 1.56 | 12.5 | 0.78 |
| Coliform | 9/70 | 3.12 | 3.12 | 0.39 |
| Coliform | 10/70 | 3.12 | 3.12 | 0.78 |
| Coliform | 17/70 | 3.12 | 0.78 | 0.39 |
| Proteus mirabilis | 35895 | 25 | 0.78 | 0.39 |
| Proteus vulgaris A | | 0.78 | 0.19 | 0.08 |
| Proteus vulgaris B | | 50 | 1.56 | 0.78 |
| Proteus | 12/70 | 100 | 3.12 | 0.78 |
| Proteus | 13/70 | 100 | 3.12 | 0.78 |
| Proteus | 20/70 | >100 | >100 | 25 |

EXAMPLE 2

In vitro-effect of combinations of 6-[(hexahydro-1H-azepin-1-yl)-methyleneamino]-penicillanic acid with various penicillins Using the same technique as described in Example 1 the in vitro-activity of 6-[(hexahydro-1H-azepin-1-yl)methyleneamino]penicillanic acid (II), of various penicillins and of 1:1-combinations of II with the respective penicillin was determined against a clinically isolated coliform bacterium (No. 9/70).

| Penicillin | M.I.C. (μg/ml) | | |
|---|---|---|---|
| | I | II | 1:1 combination |
| benzylpenicillin | 25 | 3.12 | 0.78 |
| 6-(D-α-azidophenylacetamido)penicillanic acid | 50 | 3.12 | 1.56 |
| α-carboxybenzylpenicillin | 12.5 | 3.12 | 0.38 |

EXAMPLE 3

In vivo-activity of the combination of 6-(D-α-aminophenylacet amido)penicillanic acid and 6-[(hexahydro-1H-azepin-1-yl)methyleneamino]penicillanic acid Groups of 10 animals of female NMRI white mice, 17–19 g, were given intraperitoneally inocula of the test bacterium E. coli III and immediately afterwards treated subcutaneously wth the appropriate diluted aqueous solutions of 6-(D-α-aminophenylacetamido)-penicillanic acid (I), 6-[(hexahydro-1H-azepin-1-yl)methyleneamino]penicillanic acid (II) and of a 1:1 combination (III) of the two compounds. The number of deaths in the various groups were recorded after 96 hours and the mean curative doses ($CD_{50}$) were calculated. (In the table, $LD_{50}$ gives the dilution of an overnight culture of the organism causing a 50% death rate in animals receiving no therapy; the number of $LD_{50}$-doses records the severity of the infections given to the animals.)

| $LD_{50}$ | $LD_{50}$-doses given | $CD_{50}$ (mg/kg) | | |
|---|---|---|---|---|
| | | I | II | III |
| $1.5 \cdot 10^{-3}$ | 6.6 | 5.5 | 2.0 | 1.0 |
| $8.1 \cdot 10^{-4}$ | $1.2 \cdot 10^4$ | 250 | >500 | 210 |

EXAMPLE 4

In vitro-effect of the combination of 6-(D-α-amino phenylacetamido)penicillanic acid and 6[(piperidyl-1)methyl eneamino]penicillanic acid Using the technique described in Example 1, the in vitro activity of 6-(D-α-aminophenylacetamido)penicillanic acid (I), 6-[(piperidyl-1)-methyleneamino]penicillanic acid (IV) and of a combination (V) of equal parts of the two compounds against clinically isolated enterobacteria was determined in serial dilution tests.

| Microorganism | Strain No. | M.I.C. (μg/ml) | | |
|---|---|---|---|---|
| | | I | IV | V |
| Coliform | 3/70 | 3.12 | 3.12 | 0.78 |
| | 7/70 | 3.12 | 1.56 | 0.78 |
| | 8/70 | 3.12 | 6.25 | 0.78 |
| | 14/70 | 6.25 | 3.12 | 1.56 |
| | 16/70 | 3.12 | 1.56 | 0.78 |
| | 17/70 | 6.25 | 1.56 | 0.78 |
| Proteus | 4/70 | 1.56 | 25 | 0.78 |
| | 6/70 | 0.39 | 3.12 | 0.18 |
| | 7/70 | 1.56 | 50 | 0.78 |
| | 9/70 | 6.25 | 100 | 1.56 |
| | 10/70 | 1.56 | 25 | 0.78 |
| Klebsiella- | 1/70 | 50 | >100 | 3.12 |
| Enterobacter. | 2/70 | 25 | 12.5 | 3.12 |
| | 5/70 | 100 | >100 | 12.5 |
| | 7/70 | >100 | >100 | 100 |
| | 9/70 | 50 | 3.12 | 1.56 |
| | 10/70 | 50 | >100 | 25 |
| | 431 | 100 | >100 | 12.5 |

EXAMPLE 5

In vitro-effect of combination of 6[(piperidyl-1)-methyl eneamino]penicillanic acid (IV) with various penicillins Using the same technique as described in Example 1 the in vitro activity of 6[(piperidyl-1)-methyleneamino]-penicillanic acid (IV), of various penicillins, and of 1:1 combinations of IV with these penicillins, was determined against a clinically isolated coliform bacterium.

| Penicillin | M.I.C. (μg/ml) | | |
|---|---|---|---|
| | — | IV | 1:1 combination |
| Benzylpenicillin | 25 | 6.25 | 1.56 |
| 6-(D-α-azidophenylacet-amido)penicillanic acid | 50 | 6.25 | 1.56 |
| α-Carboxybenzylpenicillin | 12.5 | 6.25 | 1.56 |

EXAMPLE 6

Emergence of resistance for E. coli III against 6-(D-α-amino-phenylacetamido)penicillanic acid, 6-[(piperidyl-1)-methyleneamino]penicillanic acid, and a 1:1 combination of the two compounds Subculturing using a serial twofold broth dilution technique was performed with 6-(D-α-aminophenylacetamido)penicillan ic acid (I), 6-[(piperidyl-1)methyleneamino]penicillanic acid (IV) and a 1:1 combination of I+IV. As inocula were used bacteria from the tube with the highest concentration of compound still permitting visible growth to the naked eye after incubation at 37° C. overnight. The following increases in MIC-values were noted.

| Passage | MIC (μg/ml) | | |
|---|---|---|---|
| | I | IV | I + IV |
| 0 | 1.56 | 0.78 | 0.38 |
| 1 | 6.25 | 6.25 | 1.56 |
| 2 | 25 | 6.25 | 0.78 |
| 3 | 50 | 25 | 0.78 |
| 4 | 50 | 25 | 1.56 |
| 5 | 100 | 25 | 3.12 |
| 6 | 100 | 25 | 3.12 |

EXAMPLE 7

Emergence of resistance for a coliform microorganism against 6-(D)-α-aminophenylacetamido)penicillanic acid, 6-[(hexahydro-1H-azepin-1-yl)methyleneamino]penicillanic acid and a combination of the two compounds Subculturing using a serial twofold broth dilution technique was performed with 6-(D-α-aminophenylacetamido)penicillanic acid (I), 6-[(hexahydro-1H-azepin-1-yl) methyleneamino]penicillanic acid (II), and a 1:1 combination of I and II. The strain used was a clinically isolated coliform. As inocula were used bacteria from the tube with the highest concentration of compound still permitting visible growth to the naked eye after incubation at 37° C. overnight. The following increases in MIC values were noted.

| Passage | MIC (μg/ml) | | |
|---|---|---|---|
| | I | II | I + II |
| 0 | 1.56 | 0.39 | 0.38 |
| 1 | 3.12 | 6.25 | 0.78 |
| 2 | 3.12 | 25 | 0.38 |
| 3 | 6.25 | 25 | 0.78 |
| 4 | 6.25 | 25 | 0.78 |
| 5 | 6.25 | 25 | 0.78 |
| 6 | 6.25 | 12.5 | 1.56 |
| 7 | 12.5 | 25 | 1.56 |
| 8 | 12.5 | 25 | 1.56 |

EXAMPLE 8

In vitro effect of the combination of cephalotin and 6-[(N,N-diethylforamidino)-N'-amino]penicillanic acid Using the technique described in Example 1 the in vitro activity of cephalotin (VI) and 6-[(N,N-diethylformamidino)-N'-amino]penicillanic acid (VII) and of a combination of equal parts of the compounds against clinically isolated strains of Coliforma and Klebsiella-Enterobacter was determined in serial dilution tests.

| Microorganism | Strain No. | MIC (μg/ml) | | |
|---|---|---|---|---|
| | | VI | VII | VI + VII |
| Coliforma | 3 | 6.25 | 6.25 | 1.56 |
| | 7 | 12.5 | 6.25 | 1.56 |
| | 14 | 12.5 | 12.5 | 6.25 |
| | 16 | 6.25 | 6.25 | 3.12 |
| Klebsiella-Enterobacter | 5 | 25 | >100 | 12.5 |

EXAMPLE 9

In vitro effect of combinations of 6-(D-α-aminophenylaceta mido)penicillanic acid and 6-[(N,N-diethylformamidino)-N'-amino]penicillanic acid Using the technique described in Example 1 the in vitro effect of combinations of 6-(D-α-aminophenylacetamido)peni cillanic acid (I) and 6-[(N,N-diethylformamidino)-N'-amino]penicillanic acid (VII) in the ratios 1:1, 1:2 and 2:1 against clinically isolated strains of Coliforma, Klebsiella-Enterobacter and Proteus was determined in serial dilution tests.

| Micro-organism | Strain No. | I | VII | I + VII 1:1 | I + VII 1:2 | I + VII 2:1 |
|---|---|---|---|---|---|---|
| Coliforma | 1 | 1.56 | 3.12 | 1.56 | 0.39 + 0.78 | 0.78 + 0.39 |
|  | 4 | 3.12 | 3.12 | 3.12 | 0.78 + 1.56 | 1.56 + 0.78 |
|  | 7 | 1.56 | 6.25 | 3.12 | 0.78 + 1.56 | 0.78 + 0.39 |
|  | 13 | 3.12 | 12.5 | 3.12 | 0.78 + 1.56 | 0.78 + 0.39 |
|  | 16 | 3.12 | 6.25 | 1.56 | 0.78 + 1.56 | 0.78 + 0.39 |
| Klebsiella-Enterobacter | 1 | 50 | >100 | 12.5 | 6.25 + 12.5 | 12.5 + 6.25 |
|  | 5 | 100 | >100 | 12.5 | 6.25 + 12.5 | 12.5 + 6.25 |
|  | 7 | >100 | >100 | 50 | 25 + 50 | 100 + 50 |
|  | 8 | 25 | 12.5 | 25 | 1.56 + 3.12 | 6.25 + 3.12 |
| Proteus | 9 | 3.12 | 100 | 3.12 | 3.12 + 6.25 | 1.56 + 0.78 |

EXAMPLE 10

In vitro effect of combinations of 6-[(hexahydro-1H-azepin-1-yl)methyleneamino]penicillanic acid with various cephalosporins Using the same technique as described in Example 1 the in vitro activity of 6-[(hexahydro-1H-azepin-1-yl) methyleneamino]penicillanic acid (II), of various cephalosporins previously mentioned in this specification, and of 1:1 combinations of II with these cephalosporins was determined against a clinically isolated strain of Klebsiella-Enterobacter (strain 4/71)

| Cephalosporin | M.I.C. (μg/ml) — | II | 1:1 combination |
|---|---|---|---|
| Cephacetrile | 50 | >100 | 50 |
| Cephazoline | 12.5 | >100 | 6.25 |
| Cephalotine | 50 | >100 | 6.25 |
| Cephalexine | 50 | >100 | 6.25 |
| Cephaloridine | 25 | >100 | 3.12 |
| EPC 807 2/b | >100 | >100 | 12.5 |
| EPC 825/1 | >100 | >100 | 25 |
| EPC 820/1b | >100 | >100 | 25 |
| EPC 821/4II | 100 | >100 | 6.25 |

EXAMPLE 11

In vitro effect of combinations of 6-[(hexahydro-1H-azepin-1-yl)methyleneamino]penicillanic acid with various cephalosporins Using the same technique as described in Example 1 the in vitro activity of 6-[(hexahydro-1H-azepin-1-yl) methyleneamino]penicillanic acid (II), of various cephalosporins and of 1:1 combinations of II with these cephalosporins was determined against a clinically isolated strain of Proteus (*Mirabilis* I 190).

| Cephalosporin | M.I.C. (μg/ml) — | II | 1:1 combination |
|---|---|---|---|
| Cephacetrile | 12.5 | >100 | 3.12 |
| Cephazoline | 6.25 | >100 | 0.78 |
| Cephalothine | 3.12 | >100 | 0.78 |
| Cephalexine | 25 | 100 | 1.56 |
| Cephaloridine | 6.25 | 100 | 0.78 |
| EPC 807 2/b | 25 | >100 | 3.12 |
| EPC 825/1 | 25 | >100 | 1.56 |
| EPC 820/1b | 50 | >100 | 6.25 |
| EPC 821/4II | 12.5 | >100 | 1.56 |

We claim:

1. A method of treating bacterial infections in a body which comprises forming an antibacterially effective 1:1 mixture of:

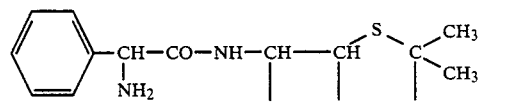

and

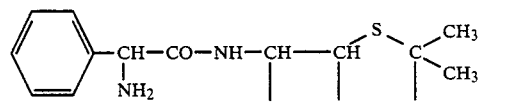

in the body.

2. A method of treating bacterial infections in a body which comprises forming an antibacterially effective 1:1 mixture of:

and in the body.